United States Patent [19]

Prince

[11] Patent Number: 4,591,505

[45] Date of Patent: May 27, 1986

[54] PROCESS FOR INACTIVATING HEPATITIS B VIRUS

[75] Inventor: Alfred M. Prince, Pound Ridge, N.Y.

[73] Assignee: New York Blood Center, Inc., New York, N.Y.

[21] Appl. No.: 581,528

[22] Filed: Feb. 21, 1984

Related U.S. Application Data

[62] Division of Ser. No. 368,250, Apr. 14, 1982, Pat. No. 4,481,189.

[51] Int. Cl.$^4$ .............................................. A61K 35/16
[52] U.S. Cl. ..................................... 424/101; 435/236
[58] Field of Search .............................. 424/101, 177; 260/112 R

[56] References Cited

U.S. PATENT DOCUMENTS 4,105,650  8/1978  Shanbrom ........................... 424/101

*Primary Examiner*—Sam Rosen
*Attorney, Agent, or Firm*—Sprung Horn Kramer & Woods

[57] ABSTRACT

A mammalian blood plasma or plasma derivative substantially free of active hepatitis B or non-A, non-B viruses is disclosed, the plasma being characterized by the presence of factor VIII, the percent by weight of denatured factor VIII to the sum of undenatured factor VIII and denatured factor VIII being less than 50%. The plasma is sterilized by contact with a detergent, alcohol or ether, and mixtures thereof and preferably a mixture of detergent and ether, usually followed by removal of the viral sterilizing agent.

11 Claims, 2 Drawing Figures

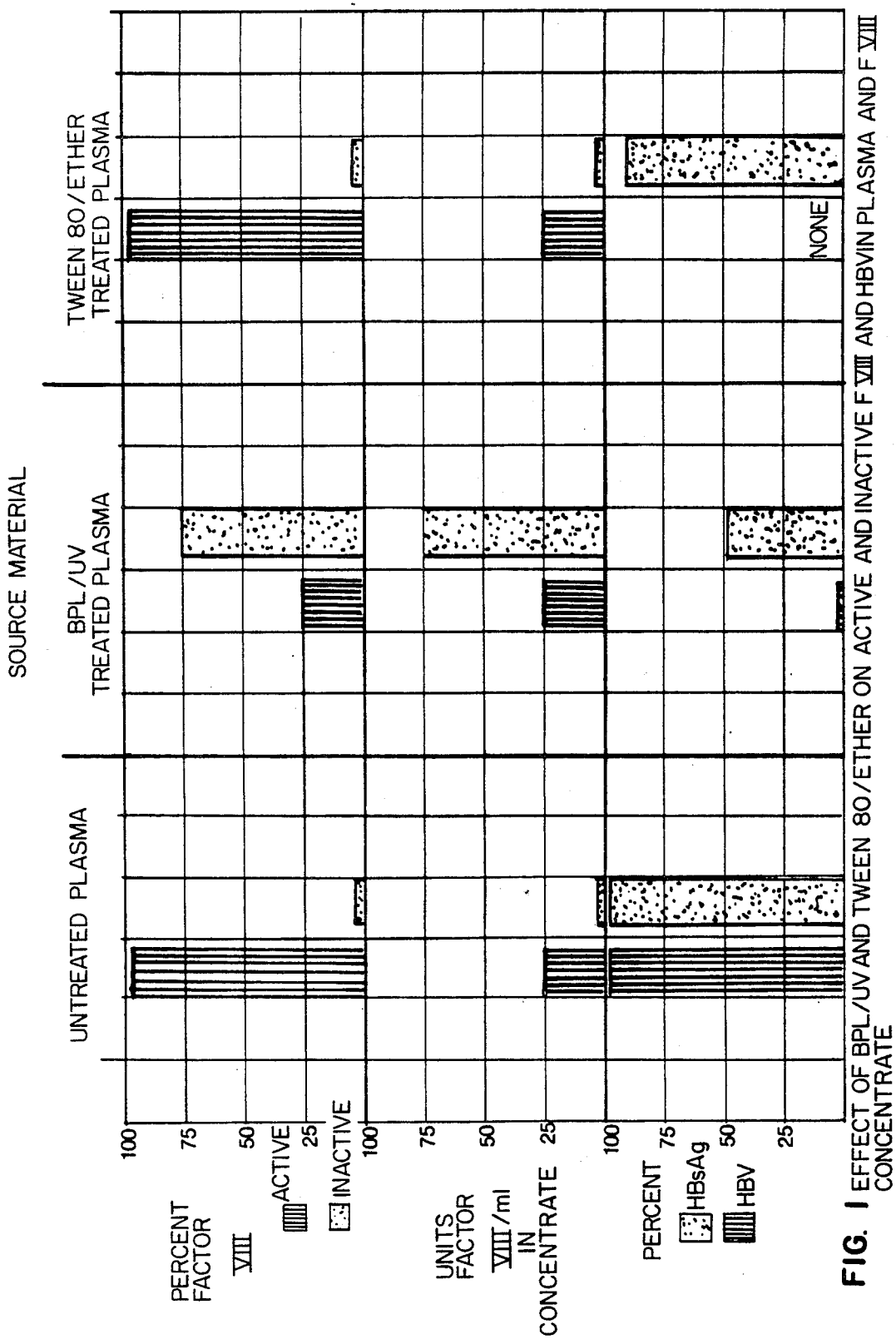
FIG. 1 EFFECT OF BPL/UV AND TWEEN 80/ETHER ON ACTIVE AND INACTIVE F VIII AND HBV IN PLASMA AND F VIII CONCENTRATE

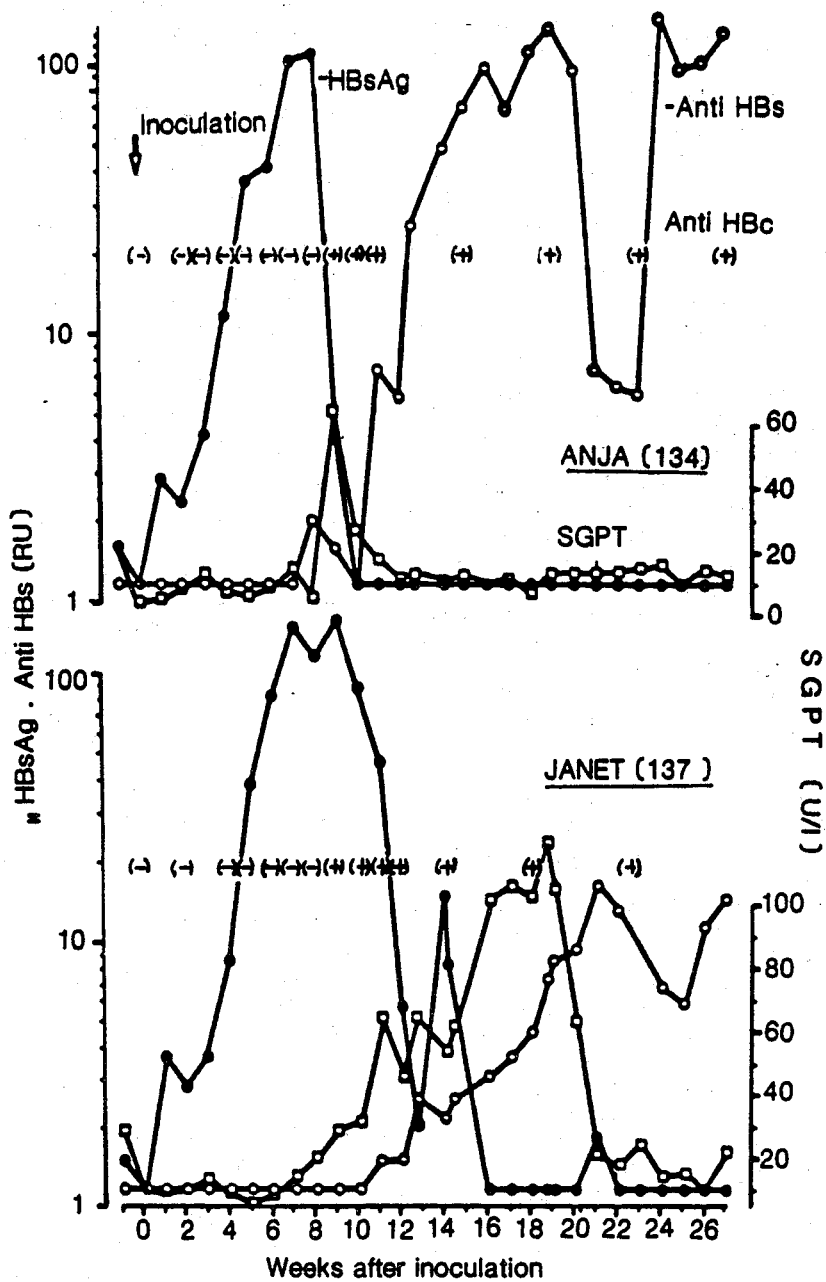
LEGEND FOR FIG. 2
RESULTS OF FOLLOW-UP OF CHIMPANZEES No. 134 AND 137 AFTER INOCULATION WITH $10^{-2}$ DILUTION OF UNTREATED HBV INFECTIVE PLASMA (No. 78-564) CLOSED CIRCLES: HBsAg, OPEN CIRCLES: ANTI-HBs, SQUARES: SGPT (ALANINE AMINOTRANSFERASE, ALT) (-): NEGATIVE TEST FOR ANTI-HBc, (+): POSITIVE TEST FOR ANTI-HBc.

PROCESS FOR INACTIVATING HEPATITIS B VIRUS

This is a division of application Ser. No. 368,250, filed Apr. 14, 1982, now U.S. Pat. No. 4,481,189.

BACKGROUND OF THE INVENTION

Field of the Invention

This invention relates to mammalian blood plasma. More especially, this invention relates to the inactivation of hepatitis B or non-A, non-B viruses in human blood plasma and to the resultant products. In particular, this invention relates to the sterilization of blood plasma to render it virtually free of active hepatitis viruses, such that the valuable proteins present therein, such as factor VIII are not appreciably denatured.

DISCUSSION OF THE PRIOR ART

Numerous attempts have been made to inactivate viruses such as hepatitus B virus (HBV) in mammalian, especially human blood plasma. It is the practice in some countries to effect inactivation of the hepatitis B virus in the blood plasma by contacting the plasma with a viral inactivating agent of the type which cross-links with the proteinaceous portion of hepatitis B virus, or which interacts with the nucleic acid of the virus. For instance, it is known to attempt to inactivate hepatitis B virus by contact with an aldehyde such as formaldehyde whereby crosslinking to the protein is effected and the hepatitis B virus is inactivated. It is also known to effect inactivation of the virus by contact with β-propiolactone (BPL), an agent which acts on the nucleic acid of the virus. It is further known to use ultra violet light, especially after a β-propiolactone treatment.

Unfortunately, these agents have only a limited ability to inactivate the viruses, and also have a deleterious effect upon other valuable protein components of the plasma. For instance, in such inactivation procedures, factor VIII is inactivated or denatured to the extent of 50–90% or more of the factor VIII present in the untreated plasma. Because of the denaturing effects of these virus inactivating agents, it is necessary in the preparation of derivatives for administration to patients to concentrate large quantities of plasma so that the material to be administered to the patient once again has a sufficient concentration of the undenatured protein for effective therapeutic treatment. This concentration, however, does not affect reduction of the amount of denatured protein. As a result, the patient not only receives the undenatured protein but a quantity of denatured protein often many times that of the undenatured protein.

For instance, if in the inactivation of hepatitis B virus in human blood plasma by β-propiolactone, there is obtained as a result thereof, a plasma whose factor VIII has been 75% inactivated, the remaining 25% of the factor VIII is therefore present in such a small concentration, as a function of the plasma itself, that it is necessary to concentrate large quantities of the factor VIII to provide sufficient concentration to be of therapeutic value. Since such separation techniques do not efficiently remove denatured factor VIII from undenatured factor VIII, the material administered to the patient may contain more denatured protein than undenatured protein. Obviously, such inactivation is valuable from a standpoint of diminishing the risk of hepatitis B virus infection, however it requires the processing of large quantities of plasma and represents significant loss of valuable protein components. Furthermore, administration of large amounts of denatured proteins may render these antigenic to the host and thus give rise to autoimmune diseases, e.g. rheumatoid arthritis, or antibody to the denatured factor VIII itself.

The loss of these valuable protein components is not limited to factor VIII, the most labile of the valuable proteins in mammalian blood plasma. Similar protein denaturation is experienced in respect to the following other valuable plasma components; Coagulation factors II, VII, IX, X, Plasmin Fibrinogen, IgM, etc.

Factor VIII, however, is denatured to a larger extent that the other valuable proteins present in blood plasma.

As a result of the foregoing, except in the processing of serum albumin and stable plasma protein solution which can withstand pasteurization, it is currently the practice in the United States in respect of the processing of blood plasma and its derivatives to take no step in respect of the sterilization of the plasma for inactivation of the hepatitis viruses. As a result, recipients of factor VIII, gamma globulin, factor IX, Fibrinogen etc., must accept the risk that the valuable protein components being administered may be contaminated with hepatitis viruses. As a result, these recipients face the danger of becoming infected by these viruses and having to endure the damage which the virus causes to the liver and consequent incapacitation and illness, which may lead to death.

The BPL/UV inactivation procedure discussed above has not so far been adopted in the United States for numerous reasons, one of which lies in the fact that many researchers believe that BPL is itself deleterious since it cannot be removed completely following the inactivation and thus may remain in plasma and plasma derivatives in more than negligible amounts. BPL has been shown to be carcinogenic in animals.

Other methods for the inactivation of hepatitis B virus in the plasma are known but are usually impractical. One method involves the addition of antibodies to the plasma whereby an immune complex is formed. The expense of antibody formation and purification add significantly to the cost of the plasma production; furthermore, there is no assurance that a sufficient quantity of hepatitis B or non-A, non-B virus is inactivated. There is currently no test for non-A, non-B antibodies (although there is a test for the virus), hence, it is not possible to select plasma containing high titers of anti non-A, non-B antibody.

It is to be understood that the problems of inactivation of hepatitis viruses in plasma are distinct from the problems of inactivation of the viruses themselves due to the copresence of the desirable proteinaceous components of the plasma. Thus, while it is known how to inactivate the hepatitis B virus, crosslinking agents, e.g. glutaraldehyde, nucleic acid reacting chemicals e.g. BPL or formaldehyde, or oxidizing agents e.g. chlorox etc, it has been believed that these methods are not suitable for the inactivation of the virus in plasma due to the observation that most of these activating agents (sodium hypochlorite, formaldehyde, β-propiolactone) denature the valuable proteinaceous components of the plasma.

It, therefore, became desirable to provide a process for the sterilization of mammalian blood plasma which does not substantially denature the valuable components of the plasma and which does not entail the use of a potentially carcinogenic agent. More especially, it is desirable to provide blood plasma in which all of the hepatitis viruses present are inactivated and in which denatured protein such as factor VIII accound for only a small amount of the total amount of these proteins in the plasma.

A further advantage of the proposed procedures is the fact that plasma, or plasma protein solutions so treated become totally clear and transparent as a result of the removal of plasma lipids. Furthermore, the clarity is maintained indefinitely on storage at 4° C. This has important advantages over untreated plasma or plasma protein solutions in that:

(1) it becomes easy to detect bacterial contamination by inspection, a procedure which is difficult in turbid suspensions; and (2) development of microaggregates of precipitated lipoproteins which occurs normally on cold storage of untreated plasma or plasma protein solutions, is prevented, thus avoiding the potentially adverse effects of infusion of such microaggregates which may lodge in pulmonary, renal, or cerebral capillaries and obstruct them.

Finally, the proposed procedures permit the inactivation of viral infectivity in source plasma from chronic carriers of hepatitis B virus used for preparation of HBV viral vaccines, permitting a safer manufacturing process and a safer product. The rationale and concepts described above are illustrated in FIG. 1.

SUMMARY OF THE INVENTION

It has now been discovered, quite surprisingly, that while most of the viral inactivating agents denature factor VIII and other valuable blood plasma proteins, that not all viral inactivating agents have such effect. It has been discovered that if the blood plasma is treated with a composition selected from the group consisting of nonanionic detergents, some alcohols, ethers or a mixture thereof, that the hepatitis viruses present in the plasma are virtually entirely inactivated without substantial denaturation of other proteins. In particular, it has been discovered that by contacting the plasma with such nonanionic detergent, alcohols, ethers, or mixtures thereof, followed by removal of the inactivating agents, that both hepatitis B and non-A, non-B viruses are substantially inactivated and that the weight percent of denatured factor VIII in the plasma is less than 30%–50% based upon the combined amount of denatured and undenatured factor VIII therein. Prior to treatment pooled human blood plasma usually has an active hepatitis B virus content between $10^1$ virus particles per milliliter and $10^3$ virus particles per milliliters as well as substantial ($10^1$–$10^2$) amounts of non-A, non-B virus particles. After treatment, no living virus particles remain.

By such procedures there is provided a mammalian blood plasma characterized by the presence of factor VIII wherein the percent by weight of denatured factor VIII to the sum of undenatured factor VIII and denatured factor VIII is less than 30%–50%, said plasma containing no hepatitis B or non-A, non-B viruses.

Preferably, the mammalian blood plasma contains less than 50% by weight of denatured factor VIII based upon the sum of denatured and undenatured factor VIII present therein. More especially, it is preferred that this value be less than 15 and still more especially, less than 10% by weight. By suitable processing, one can reduce the weight percent of denatured factor VIII to less than 5%, especially less than 3%, more especially less than 2% by weight based upon the combined weight of denatured and undenatured factor VIII.

By the inactivation procedure of the invention, virtually all of the hepatitis viruses contained therein are inactivated. The method for determining infectivity levels by in vivo tests on chimpanzees is discussed by Prince, A. M., Stephen W., Brotman B and van den Ende M. C., Evaluation of the effect of Betapropiolactone/Ultraviolet Irradiation (BPL/UV) Treatment of Source Plasma on Hepatitis Transmission by factor IV Complex in Chimpanzees, Thrombosis and Haemostasis 44: 138-142, 1980.

The inactivated hepatitis virus is inactivated by treatment with the specifically contemplated inactivating agents described herein, and is not inactivated because of inclusion in the plasma of antibodies which bind with the hepatitis viruses and form immune complexes; although this may occur also.

Treatment of plasma involves addition of a nonionic detergent, ether, alcohol, or mixture thereof. As a result of this treatment, there may remain a small residual amount of such nonionic detergent, ether, or alcohol. Therefore, blood plasma of the invention can be characterized by containing a residual amount of nonionic detergent, ether or alcohol but such nonionic detergent, ether or alcohol is present in a concentration of less than 1%, preferably less than 0.001%.

By the treatment of the invention, plasmas obtained from donors can be pooled without special precautions to insure that plasma containing active hepatitis B virus is not added to the pool. This facilitates the processing of the plasma and enables elimination of several steps, including early testing of each pint of blood received from the donor. It permits processing of large quantities of plasma with attendant savings in costs.

During processing of plasma hepatitis viruses are inactivated by treatment with a nonanionic detergent, alcohol, or ether, or a mixture thereof. Preferably, there is employed a mixture of a detergent and either or both of an alcohol and an ether. Generally speaking, the treating agent preferably comprises 0.1 to 10% by weight detergent based upon the volume of plasma or plasma derivatives to be treated. In particular, it is contemplated that the use of a treating agent comprising a mixture of detergent and ether where the detergent is present in the composition in an amount of 0.1 to 10%, preferably 0.1 to 1.0%, based upon the volume of plasma or plasma derivative to be treated.

The ether, or alcohol can be added in an amount of 5 to 50%, preferably 20 to 40% by volume, based on the volume of plasma or plasma derivatives to be treated.

Generally speaking the pH of the inactivating agent solution, dispersion, or suspension, is from 6.0 to 8.0.

Particularly contemplated ethers for use inactivation in accordance with the invention are those having the formula

wherein $R^1$ and $R^2$ are independently $C_1$–$C_{18}$ alkyl or alkenyl which can contain an O or S atom in the chain, preferably $C_1$–$C_8$ alkyl or alkenyl. Especially contemplated ethers are dimethyl ether, diethyl ether, ethyl propyl ether, methyl-butyl ether, methyl isopropyl ether and methyl isobutyl ether.

Alcohols contemplated include those of the formula $R^3OH$ wherein $R^3$ is a $C_1$ to $C_{18}$ alkyl or alkenyl radical which can contain 1 or more oxygen or sulphur atoms in the chain and which can be substituted by one or more hydroxyl groups.

Especially contemplated alcohols are those where the alkyl or alkenyl group is between 1 and 8 carbon atoms. Particularly contemplated alcohols include methanol, ethanol, propanol, isopropanol, n-butanol, isobutanol, n-pentanol and the isopentanols. Also contemplated are compounds such as ethylene glycol, 1,2-propylene glycol, 1,3-propane diol, 1,4-butanediol, 1,3-butanediol, 2-hydroxy isobutanol (2-methyl, 1,2-dihydroxypropane).

Contemplated nonionic detergents include those which disperse at the prevailing temperature up to 0.1% by weight fat in an aqueous solution containing 0.1% by weight fat when 1 gram per 100 ml of detergent is introduced therein. In particular there is contemplated detergents which include polyoxyethylene derivatives of fatty acids, partial esters of sorbitol anhydrides, for example, those products known commercially as Tween 80 and Tween 20 nonionic oil soluble water soluble detergent such as that sold commercially under the trademark "Triton X 100". Also contemplated is sodium deoxycholate as well as the "Zwittergents" which are synthetic zwitterionic detergents known as "sulfobetaines" such as N-dodecyl-N,N-dimethyl-2-ammonio-1-ethane sulphonate and its congeners or non-ionic detergents such as octyl-beta-D-glucopyranoside.

Other contemplated non-ionic detergents are those having about 15 to about 35, preferably about 18 to 33, oxyethylene units in the molecule, especially in the presence of a mercaptan reducing agent, such as, for example, mercaptoethanol, dithiothreitol, dithioerythritol, and dithiooctanoic acid. Suitable nonionic surfactants are oxyethylated alkyl phenols, polyoxyethylene sorbitan fatty acid esters, polyoxyethylene acids, polyoxyethylene alcohols, polyoxyethylene oils and polyoxyethylene oxypropylene fatty acids. Some specific examples are the following:

alkylphenoxypolyethoxy (30) ethanol
polyoxyethylene (2) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) lauryl ether
polyolyethylene (20) cetyl ether
polyoxyethylene (20) stearyl ether
polyoxyethylene (20) oleyl ether
polyolyethylene (25) hydrogenated castor oil
polyoxyethylene (25) oxypropylene monostearate.

Treatment of plasma with the inactivating agent is effected at a temperature between $-5°$ C. and $50°$ C., preferably between $1°$ and $4°$ C. for at least 1 minute, preferably at least 16 hours and generally 16 to 24 hours. The treatment is normally effective at atmospheric pressure although subatmospheric and superatmospheric pressures can also be employed.

Normally, after the treatment, the virus inactivating agent is removed although such is not necessary in all instances, depending upon the nature of the virus inactivating agent and the intended further processing of the plasma.

To remove ether from the plasma the plasma is generally subjected to a temperature of $4°$ to $37°$ C. with a slight vacuum imposed to draw off residual ether. Preferably means are provided to spread the plasma as a thin film to insure maximum contact and removal of the ether. Other methods for removal of ether in activating agents include:

(1) bubbling of nitrogen gas;
(2) diafiltration using ether insoluble (e.g. teflon) microporous membranes which retain the plasma proteins;
(3) absorption of desired plasma components on chromatographic or affinity chromatographic supports;
(4) precipitation e.g. by salting out of plasma proteins;
(5) lyophilization, etc.

When alcohol or nonionic detergents are employed in the inactivating agent they are removed by (2)-(5) above.

Generally speaking, any ether present is initially removed prior to removal of any detergent. The ether may be recovered for reuse by the use of suitable distillation/condensor systems well known to the art.

Alcohol is normally removed together with detergent. If the detergent includes both alcohol and ether, the ether is normally removed before the alcohol.

As described above, blood plasma can be characterized by the relative amount of denatured factor VIII to the sum of denatured and undenatured factor VIII. In particular, the weight percent of denatured factor VIII to the sum of denatured and undenatured factor VIII is less than 50%. Detection of the amount of denatured factor VIII is determined by determining the ratio between factor VIII antigen (CAG) content (a measure of factor VIII protein) and factor VIII activity (a measure of undenatured factor VIII. The ratio:

(FVIII activity/CAG antigen)

is ideally 1.0 when there is no denaturation, and should not be less than 0.5.

The above assays are carried out by standard methods, e.g., as described in *Haemostatis and Thrombosis*, A. L. Bloom, D. P. Thomas, Edw. Churchill-Livingstone, London, 1981.

The method of the invention permits the pooling of human blood plasma and the treatment of the pooled human blood plasma in the form of such pooled plasma. It also permits the realization of blood products derivatives such as factor VIII gamma globulin, factor IX or the factor IX complex (factors II VII, IX X), fibrinogen and any other blood derivative including HBsAg used for the preparation of HBV vaccine, all of which contain no residual infective hepatitis viruses. Thus this invention further contemplates the separation components of pooled plasma where each of the components is characterized by:

(a) the absence of trace amounts of a viral inactivating agent which crosslinks with the proteinaceous portion of a virus or acts upon the nucleic acid of a virus; and/or (b) the presence of detectable amounts of nonionic detergent viral inactivating agent, ether, or alcohol, but in an amount of less than 1% by weight; and/or (c) the presence of inactivated hepatitis B and/or non-A, non-B viruses; and/or (d) the absence of infective (variable) hepatitis viruses.

In order to more fully illustrate the nature of the invention and the manner of practicing the same, the following examples are presented:

EXAMPLE 1

Inactivation of Hepatitis B and Non-A, Non-B Viruses in Plasma

[A] Hepatitis B Virus

New York Blood Center Standard HBV challenge virus (plasma 78-564 obtained from a chronic carrier of the virus) was diluted 1:10 with fresh normal (chimp 222) chimpanzee plasma lacking antibody to HBsAg. This dilution contains $10^{7.9}$ chimpanzee infectious doses ($CID_{50}$) per ml. Tween 80 was added to make a final concentration of 1% V/V, and then ethyl ether. (Malinckyodt, anaesthetic grade) was added to a final concentration of 20% V/V. The solution was well mixed by vortexing, and then held at 4° C. for 16 hours. Ether was then removed under vacuum, the solutions were centrifuged for 10 min. at 4000 rpm and the clear plasma was recovered. 1.25 ml was injected intravenously into 2 seronegative chimpanzees which had never previously been used in any experiment. These were followed with weekly tests of hepatitis B serologic markers (HBsAg, anti-HBs, anti-HBc, and serum transaminase levels (AST, ALT), for 12 months. The remainder of the plasma was tested for factor VIII procoagulant activity, for factor VIII (CAG) antigen activity, and for quantity of HBsAg (the hepatitis B surface antigen). Two additional chimpanzees received the same infective plasma diluted $10^{-2}$, but untreated. The results are shown in Table I HBV inoculated into the controls, developed any indication of HBV infection, indicating that all of the infective viruses had been inactivated. The process efficacy of this procedure is thus $\geq 10^{7.9}$, i.e., at least 100 million infective doses can be inactivated. Despite this extraordinary sterilizing activity, there was virtually complete recovery of factor VIII procoagulant activity, factor VIII protein, and HBsAg. It should be noted that the maintenance of HBsAg activity indicates that this process can be used as an improved technique for preparation of hepatitis B vaccine from plasma of HBV carriers.

[B] Inactivation of Non-A, Non-B Hepatitis Virus in Plasma

This experiment was done in parallel with the above experiment and utilized identical methodology except that:

1. The infective plasma was a $10^{-1}$ dilution of HUTCHINSON STRAIN (7-12-77) Non-A, non-B virus received frozen in dry ice from Dr. Robert Purcell, head of the Hepatitis Laboratory, National Institute for Allergy & Infectious Diseases, N.I.H., Bethesda, Md. This material produces non-A, non-B hepatitis in chimpanzees with an incubation period prior to ALT elevation of about 5-7 weeks. This material has been found to have a titer of about $10^6$ $CID_{50}$/ml in chimpanzees, and about $10^8$ $ID_{50}$ in marmosets (Feinstone, S. & Purcell R. H., Personal Communication). Thus the treated plasma which contained a $10^{-2}$ dilution of the Hutchinson Plasma had an infective virus content of $10^4$–$10^6$ $ID_{50}$/ml.

2. The inoculated chimpanzees had been used previously for a safety test of formalin inactivated HBV vaccine but had not been used in any other experiment.

TABLE I

INACTIVATION OF HBV INFECTIVITY BY TWEEN 80/ETHER WITHOUT INACTIVATION OF FACTOR VIII AND HBsAg

| Chimpanzee No. | Activity HBV Dose Inoculated ($CID_{50}$) | Treatment of Plasma | Hepatitis (ALT >50 IU/L) | Incubation period to development of HBsAg (weeks) | Development of Anti-HBs and Anti-HBc | Analysis of Plasma Factor VIII* Activity (%) | Antigen (%) | HBsAg (ugm/ml)** |
|---|---|---|---|---|---|---|---|---|
| 134 | $10^{6.9}$ | none | + | 4 | + | 100 | 100 | 90 |
| 137 | $10^{6.9}$ | none | + | 4 | + | | | |
| 146 | $10^{7.9}$ | Tween 80 + Ether | (−) | (−) | (−) | 96 ± 9‡ | 95 ± 9‡ | 81 ± 18‡ |
| 163 | $10^{7.9}$ | Tween 80 + Ether | (−) | (−) | (−) | | | |

*Expressed as percent of untreated plasma
**adjusted for dilution to give content in original plasma
‡ ± 2 standard deviations Both chimpanzees receiving untreated HBV developed hepatitis B infection with an incubation period of 4 weeks. The actual results are illustrated in FIG. 2.

In marked contrast, neither animal receiving the Tween 80/ether treated HBV infective plasma, which initially contained 10 times the quantity of infective They were followed with biweekly tests for all markers listed above for 12 months. Eight control chimpanzees have been inoculated with the same Hutchinson strain inoculum and similarly followed. The results are shown in Table II.

TABLE II

Inactivation of Non-A, non-B Virus Infectivity without Inactivation of Factor VIII Activity

| Chimpanzees | NANB Virus Dose Inoculated ($10_{50}$) | Treatment | Hepatitis (Incubation Period to ALT >50) | ANALYSIS OF PLASMA: Factor VIII* Activity % | Antigen % |
|---|---|---|---|---|---|
| 8 Chimpanzees | $10^3$–$10^5$ | none | 3–21 | N.D. | N.D. |
| 157 | $10^4$–$10^6$ | Tween 80 + | (−) | 97 ± 10‡ | 98 ± 10‡ |

TABLE II-continued

| Inactivation of Non-A, non-B Virus Infectivity without Inactivation of Factor VIII Activity | | | | | |
|---|---|---|---|---|---|
| | NANB Virus Dose Inoc- | | Hepatitis (Incubation | ANALYSIS OF PLASMA: Factor VIII* | |
| Chimpanzees | ulated ($10_{50}$) | Treat- ment | Period to ALT >50) | Activity % | Antigen % |
| 164 | | Ether | (—) | | |

*expressed as percent of untreated plasma
± 2 standard deviations

Thus again the treated plasma was non-infective, yet maintained its factor VIII activity. The process efficacy for inactivation of non-A, non-B virus estimated from this experiment is $\geq 10^4-10^6$ i.e., at least 10,000–1,000,000 infective doses can be inactivated.

EXAMPLE II

Tween 80/Ether Treatment of Factor VIII Concentrated (Lyoc ®, The New York Blood Center) with Complete Maintenance of Factor VIII Procoagulant Activity Lyoc ® is a concentrate of factor VIII which is licensed for clinical use in the treatment of hemophilia. Lyoc is prepared without attempted sterilization of hepatitis viruses, and is thus probably uniformly infective to non-immune recipients. A sample of Lyoc was treated with Tween-80/ether, as described above to determine whether the contained factor VIII activity would be preserved.

The results are shown in Table III

TABLE III

| Effect of Tween 80/Ether Treatment of a Factor VIII Concentrate on Factor VIII Activity | |
|---|---|
| Material | Factor VIII Procoagulant Activity (% of Untreated) |
| Lyoc - untreated | 100 ± 10 |
| Lyoc - Tween 80/ether treated | 110 ± 10 |

There was essentially complete recovery of factor VIII activity.

The process of the invention is useful in the inactivation of other viruses present in blood such as: Cytomegaloviruses, Epstein Barr viruses, Lactic dehydrogenase viruses, Herpes group viruses, Rhabdoviruses, Leukoviruses, myxoviruses, alphaviruses, Arboviruses (group B), Paramyxoviruses, Arenaviruses and Coronaviruses.

What is claimed is:

1. A process for inactivating the hepatitis B virus in mammalian blood plasma or a concentrate therefrom which comprises contacting said blood plasma or a concentrate therefrom with effective amounts of alcohol and a virus inactivating agent selected from the group consisting of a nonionic detergent, ether and a mixture of a nonionic detergent and ether, at a temperature of between −5° C. and 50° C. and for a time of at least one minute to thereby inactivate the hepatitis B virus.

2. A process according to claim 1, wherein said plasma is contacted with an alcohol of the formula $$R^3OH$$

wherein
R$^3$ is C$_1$ to C$_{18}$ alkyl or an alkenyl group which can contain an oxygen or an sulphur atom in the chain and can be substituted by one or more hydroxy groups.

3. A process according to claim 1, wherein said contact with nonionic detergent and ether is a successive contact.

4. A process according to claim 1, wherein the alcohol and viral inactivating agent are present in an amount of at least 0.1% by weight, based on the volume of the plasma to be treated.

5. A process according to claim 4, wherein said alcohol and viral inactivating agent are present in an amount of between 0.1 and 50% by weight based upon the volume of the plasma.

6. A process according to claim 5, wherein following said treatment said alcohol and viral inactivating agent are removed.

7. A process according to claim 1, wherein said mammalian blood plasma is human blood plasma or plasma derivative.

8. A process according to claim 7, wherein said human blood plasma is pooled blood plasma or plasma derivative from such human plasma pools.

9. A process according to claim 1, wherein the blood plasma subjected to said process contains Non-A, Non-B Hepatitis virus.

10. A process according to claim 1, wherein the temperature is between 1° C. and 4° C.

11. A process according to claim 1, wherein the time is between 16 and 24 hours.

* * * * *

UNITED STATES PATENT AND TRADEMARK OFFICE
CERTIFICATE OF CORRECTION

PATENT NO. : 4,591,505
DATED : May 27, 1986
INVENTOR(S) : Alfred M. Frince

It is certified that error appears in the above-identified patent and that said Letters Patent are hereby corrected as shown below:

Col. 3, line 52     Delete "milliliters" and substitute --milliliter--

Col. 6, line 57     Delete "separation" and substitute --separate--

Col. 7, line 1     Delete "(variable)" and substitute --(viable)--

Col. 9, footnote, line 2     Before "$\pm$" insert --$\neq$--

Col. 10, line 12     Delete "virus" and substitute --viral--

Signed and Sealed this

Twenty-third Day of September 1986

[SEAL]

Attest:

DONALD J. QUIGG

Attesting Officer     Commissioner of Patents and Trademarks